United States Patent [19]
Hori

[11] Patent Number: 5,349,941
[45] Date of Patent: Sep. 27, 1994

[54] CLEANABLE ENDOSCOPE

[75] Inventor: Koichiro Hori, Framingham, Mass.

[73] Assignee: Oktas, Framingham, Mass.

[21] Appl. No.: 38,167

[22] Filed: Mar. 26, 1993

[51] Int. Cl.$^5$ .............................................. A61B 1/00
[52] U.S. Cl. ........................................ 128/4; 128/6
[58] Field of Search .................. 128/4, 6, 7, 8, 5, 10, 128/11

[56] References Cited

U.S. PATENT DOCUMENTS

| | | |
|---|---|---|
| Re. 33,854 | 3/1993 | Adair . |
| 3,835,842 | 9/1974 | Iglesias . |
| 3,850,162 | 11/1974 | Iglesias . |
| 4,072,147 | 2/1978 | Hett . |
| 4,190,041 | 2/1980 | Chikama . |
| 4,216,767 | 8/1980 | Aoshiro . |
| 4,241,729 | 12/1980 | Aoshiro . |
| 4,261,346 | 4/1981 | Wettermann . |
| 4,281,646 | 8/1981 | Kinoshita . |
| 4,288,882 | 9/1981 | Takeuchi . |
| 4,367,730 | 1/1983 | Tanaka . |
| 4,369,768 | 1/1983 | Vukovic ........................ 128/6 |
| 4,414,962 | 11/1983 | Carson ........................ 128/6 |
| 4,562,830 | 1/1986 | Yabe . |
| 4,562,831 | 1/1986 | Murakoshi et al. . |
| 4,579,598 | 4/1986 | Sasa et al. . |
| 4,646,722 | 3/1987 | Silverstein et al. . |
| 4,667,691 | 5/1987 | Sasa . |
| 4,741,326 | 5/1988 | Sidall et al. . |
| 4,742,818 | 5/1988 | Hughes et al. ................ 128/6 |
| 4,762,120 | 8/1988 | Hussein ..................... 128/6 |
| 4,854,302 | 8/1989 | Alfred, III . |
| 4,878,485 | 11/1989 | Adair . |
| 4,907,395 | 3/1990 | Opie et al. . |
| 4,979,498 | 12/1990 | Oneda et al. ............... 128/7 X |
| 4,997,084 | 3/1991 | Opie et al. . |
| 5,025,778 | 6/1991 | Silverstein et al. . |
| 5,048,508 | 9/1991 | Storz ....................... 128/4 |
| 5,188,092 | 2/1993 | White . |
| 5,188,094 | 2/1993 | Adair . |

Primary Examiner—Richard J. Apley
Assistant Examiner—Karen A. Jalbert
Attorney, Agent, or Firm—Weingarten, Schurgin, Gagnebin & Hayes

[57] ABSTRACT

An endoscope includes a handle body having first and second ends and having a channel region therein with the channel being exposed on at least one side of the handle body. A cover is disposed on the handle body with a portion of the cover disposed in over exposed region of the channel. An end piece is disposed over the first end of the handle body and a first tube having a channel provided therein is coupled to the second end of the handle body. The endoscope further includes a sheath disposed over the first tube and removably coupled to a first one of the tube and the second end of the handle body.

20 Claims, 3 Drawing Sheets

CLEANABLE ENDOSCOPE

FIELD OF THE INVENTION

This invention relates to endoscopes and more particularly to cleanable endoscopes.

BACKGROUND OF THE INVENTION

As is known in the art, a virus may be transmitted between persons due to the virus attaching to an instrument, such as an endoscope for example, used during a surgical procedure and ineffective post operative sterilization of such instruments. Such virus transmission may lead to serious infection, injury or even death of a patient. There has, therefore, been a trend to eliminate the transmission of such viruses via surgical instruments due to ineffective sterilization techniques.

In some instances, however, it may be relatively difficult to clean an instrument such as an endoscope. For example, an operative endoscope generally includes a tube having a bore of relatively small diameter extending through a generally central longitudinal axis thereof. The operative endoscope may further include electrical or optical components which are relatively delicate or fragile. Endoscopes having such delicate, fragile components may thus generally not be disposed in an autoclave and exposed to temperatures which are high enough to guarantee sterilization of the endoscope without damaging the instrument. Thus, it is relatively difficult to ensure effective sterilization of such endoscopic instruments using conventional techniques.

In addition to autoclave sterilization techniques, there exist sterilization techniques such as ETO gas sterilization, liquid sterilization and gamma ray sterilization. These techniques, however provide several drawbacks. For example, one problem with gas sterilization is that it requires a relatively long duration of time, typically in the range of about six to ten hours to insure adequate sterilization. Furthermore strict regulations exist for exhausting the resulting gas. Liquid sterilization techniques are generally not as effective as the autoclave technique in some applications and gamma ray sterilization techniques may not be used on those surgical instruments having glass therein since the gamma rays adversely effect the glass.

SUMMARY OF THE INVENTION

In accordance with the present invention, an endoscope includes a handle body having first and second ends and having a channel region therein with the channel being exposed on at least one side of the handle body. A cover is disposed on the handle body with a portion of the cover disposed over the exposed region of the channel. An end piece is disposed over the first end of the handle body and a first tube having a channel provided therein is coupled to the second end of the handle body. The endoscope further includes a sheath disposed over the first tube and coupled to a first one of the first tube and the first end of the handle body. With this particular arrangement, an endoscope which may be easily cleaned is provided. During a surgical procedure, the cover and end piece are disposed over the handle body and the sheath is disposed over the tube. After the surgical procedure terminates, the cover, end piece and sheath may each be removed to expose the corresponding portions of the handle body and tube including the instrument channel. Thus the handle body, tube and in particular the instrument channel may be effectively and more easily cleaned than in the prior art approaches. Furthermore, the sheath may be removed from the tube and may be exposed to temperatures which are high enough to guarantee sterilization of the sheath. Thus, if temperature sensitive components such as a viewing system for example are disposed in the tube such components are not damaged due to exposure to high temperature sterilization techniques. Moreover if the sheath, cover and endpiece are provided from a metal material then the sheath, cover and endpiece may be disposed in an autoclave for cleaning. Alternately, the sheath may be provided as a disposable sheath and thus need not be cleaned.

BRIEF DESCRIPTION OF THE DRAWINGS

The foregoing features of this invention as well as the invention itself may be more fully understood from the following detailed description of the drawings in which

FIG. 1A is a front view of a portion of the endoscope of FIG. 1;

DESCRIPTION OF THE PREFERRED EMBODIMENTS

Figure 1:
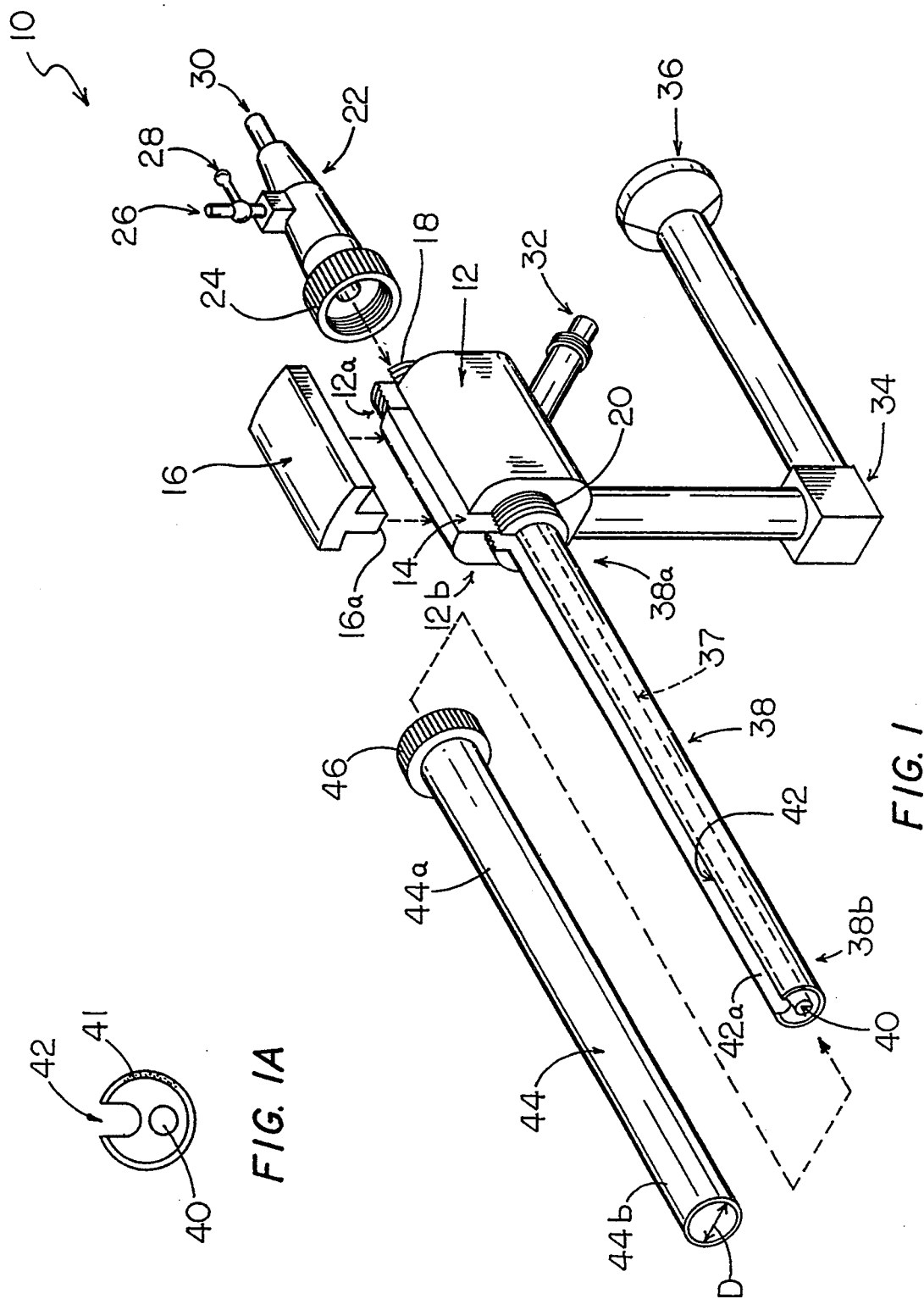
FIG. 1 is an exploded view of an endoscope.

Referring now to FIG. 1, a cleanable operative endoscope 10 includes a handle body 12 having first and second ends 12a, 12b and having a channel (cavity) region 14 therein. A handle cover 16 may be removed from the handle body 12 to thus expose the channel 14 on at least one side of the handle body 12.

The cover 16 may be disposed on the handle body 12 to provided an airtight fit between the cover 16 and the body 12. The cover is here provided having a raised portion 16a having a length and width selected to be disposed in the channel 14. Alternatively, the cover 16 could have been provided having a channel (not shown) therein into which a corresponding raised portion (not shown) of the body 12 may be disposed.

An end piece 22 is disposed on the first end of said handle body 12a. Here the first end of the handle body 12a is provided having a first threaded portion 18 and the end piece 22 is provided having a threaded portion 24 selected to mate with the threaded portion 18. It should be noted however that any means for securely fastening the end piece 22 to the handle body 12 may be used. The end piece 22 here includes a fluid injection port 26 including an infusion valve stop cock 28 for injecting fluid through the handle channel 14 and into a channel 42 formed between a first tube 38 coupled to the handle body 12 and a surrounding sheath 44 as will be described below. A fluid, such as carbon dioxide ($CO_2$) for example, may be introduced through the infusion port 26 and the flow of such fluid may be controlled by the stop cock 28. The end piece 22 is also here provided having an instrument insertion aperture 30 having a diameter selected to allow a medical instrument to be disposed therethrough and into the U channel 42 of tube 38.

The body 12 is also provided having a light guide port 32 to which a light source, such as a fiber optic light source for example, may be coupled. A viewing system 34 including an eyepiece 36 is also coupled to the body 12. The viewing system is coupled through to an optical viewing path such as a lens train and prisms (not shown) or an electronic viewing path (not shown) disposed in a viewing path 37 of the tube 38. Here, the viewing path 37 terminates at the distal end of the tube 38b in an objective lens 40. It should be recognized of course that in some applications it may be desirable to terminate the viewing path 37 in, inter alia, a window (not shown) or a prism (not shown).

Referring briefly to FIG. 1A, in which like elements of FIG. 1 are provided having like reference designations, a plurality of illumination fibers 41 are disposed in a hollow annular region 39 of the tube 38. An illumination source may be coupled to the illumination port 32 (FIG. 1) to thus feed light to the illumination fibers 41 to provide illumination during a surgical procedure for example.

Referring again to FIG. 1, the second end of the handle body 12b is provided having a second threaded portion 20. The first tube 38 has a proximal end 38a coupled to the second end of said handle body 12b. It should be recognized that cover 16, and sheath 44 may be provided as a single piece via injection molding techniques for example or alternatively the cover 16 and sheath 44 may be provided as separate pieces and fastened, respectively, on to the tube 38 and body 12. Such fastening may be accomplished using any well known fastening techniques such as threading, interference fit, snap-on assemblies, or any other suitable fastening technique well known to those of ordinary skill in the art. It is desirable to use fastening techniques which allow the cover 16 and sheath 44 to be easily and quickly attachable and removable from the corresponding portions of the endoscope 10. The manufacturing techniques may of course be selected to provide a high quality, low cost handle body 12, tube assembly 38, cover 16 and sheath 44.

The tube 38 is provided having a first predetermined length and a predetermined diameter and is provided having a bore therethrough which provides the viewing path 37. The tube 38 is also provided having the channel 42, here having a U-shaped cross-section, extending along a first surface of the tube 38 between the first and second tube ends 38a, 38b. A surgical instrument may thus be disposed in the aperture 30 of the end piece 22, through the handle channel 14, and operative channel 42 to reach the surgical sight through aperture 42a.

A sheath 44 having first and second opposing ends 44a, 44b is provided having a diameter D selected to allow the sheath 44 to be disposed over the first tube 38 and a length L selected to cover the channel 42. The sheath 44 may be disposed over the first tube 38 and coupled to the threaded handle portion 20 via the collar 46 which is here provided having threads selected to correspond to the threaded handle portion 20. It should be noted that threaded region 20 has here been provided as a portion of the handle body 12 however it should be appreciated that the threaded region 20 may alternatively have been provided as part of the first tube 38. Furthermore, the threaded region 20 and corresponding threads on sheath 44 may have been provided at the ends 38b and 44b respectively. It should also be understood that the sheath 44 may be disposed over the tube 38 and securely held in place using any removable coupling or fastening means well known to those of ordinary skill in the art including but not limited to clamping mechanisms, latching mechanisms, snap-on mechanisms, screws, bolts or the like.

The sheath 44 may be provided from metal, plastic or any other material suitable for surgical applications. Furthermore the infusion port 26 may be disposed in the protective sheath 44 or cover 16 rather than in the end piece 22. The infusion port may be disposed on any of the three members. The particular selection of where to provide the infusion port may be made in accordance with a variety of factors including but not limited to the disposability and autoclavability of the cover 16, end piece 22 and protective sheath 44.

For example, if the endpiece 22 were made from a material which may withstand an autoclave cleaning procedure such as metal for example, the infusion stop cock 26 should preferably also be made from a material which is autoclavable. Alternatively, the stop cock 26 may be made from a disposable material such as plastic, for example, and attached onto another disposable part such as the cover 16 or sheath 44 if those pieces were also made from a disposable material such as plastic. Another alternative may be provided by manufacturing the end piece 22 and stop cock 26 from a disposable material such as plastic.

During a surgical procedure, the endoscope 10 is provided having the cover 16 and end piece 22 disposed over the handle body 12 and the sheath 44 disposed over the tube 38. After the surgical procedure terminates, the cover 16, end piece 22 and sheath 44 may be removed to expose the corresponding portions of the handle body 12 and tube 38 including the instrument channel 42. Thus the handle body 12 and tube 38 and in particular the instrument channel 42 may be effectively and more easily cleaned than in the prior art approaches.

Furthermore, the cover 16, end piece 22 and sheath 44 may be removed from the endoscope instrument and may be exposed to temperatures which are high enough to guarantee sterilization of the cover 16, end piece 22 and sheath 44 without damaging the more delicate portions of the endoscope such as the viewing system 40. Moreover if the cover 16, end piece 22 and sheath 44 are provided from a metal material then these pieces may be disposed in an autoclave for cleaning. Alternately, the cover 16, end piece 22 and sheath 44 may be provided as a disposable pieces and thus need not be cleaned.

Figure 2:
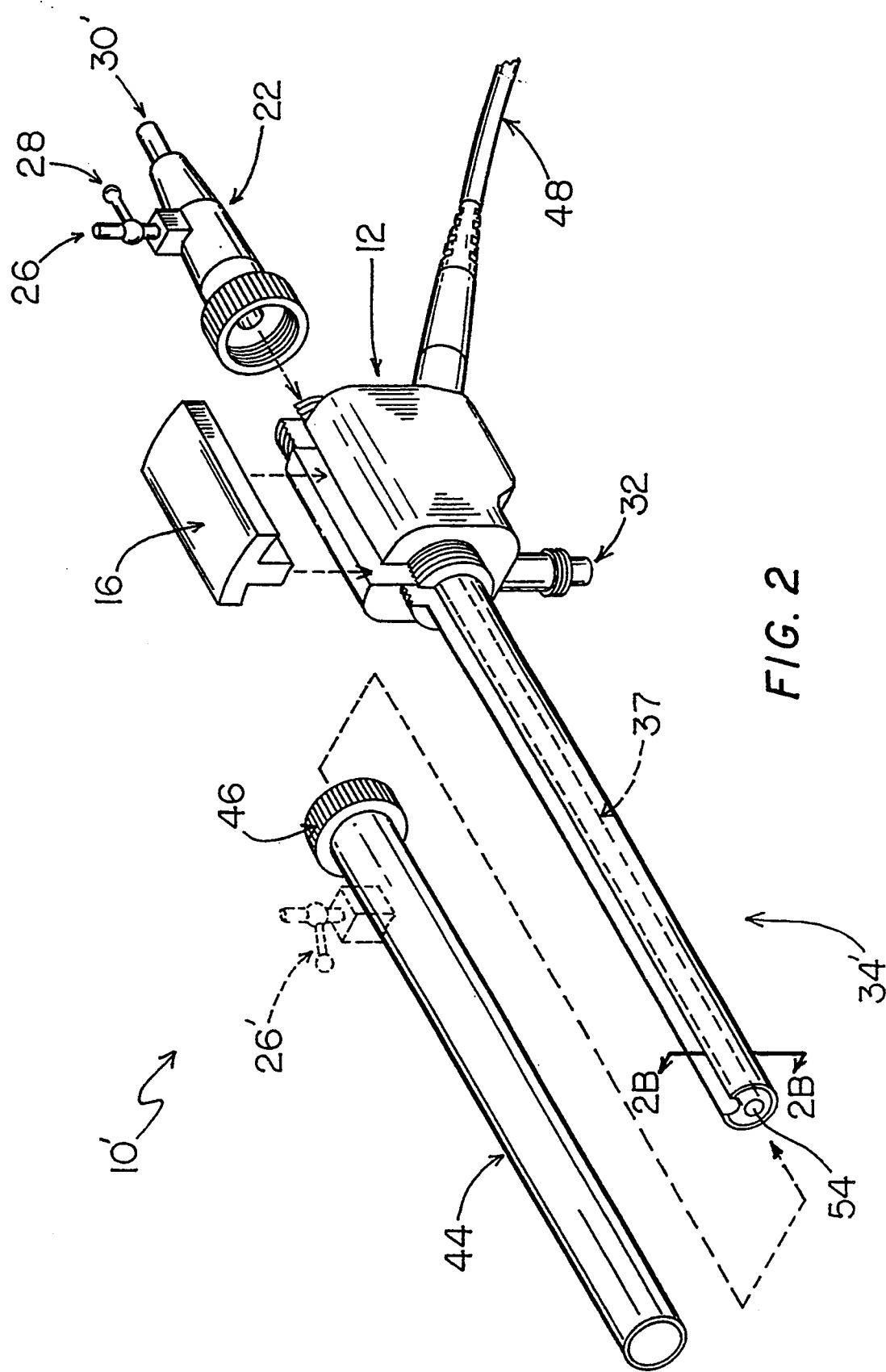
FIG. 2 is an exploded view of an endoscope having an electronic viewing system.
Figure 2A:
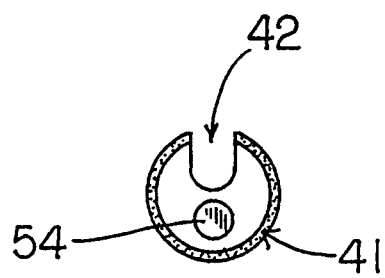
FIG. 2A is a front view of a portion of the endoscope of FIG. 2.
Figure 2B:
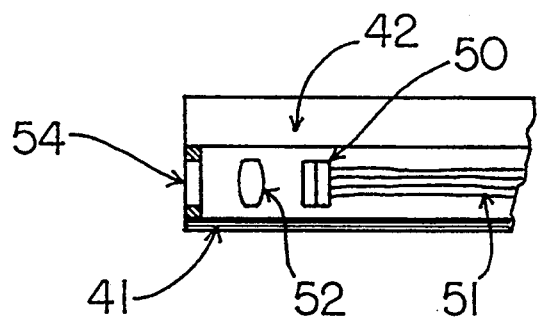
FIG. 2B is a side view of a portion of the endoscope of FIG. 2.

Referring now to FIGS. 2–2B in which like elements of FIGS. 1 and 1A are provided having like reference designations, an endoscope 10' is provided having an electronic viewing system 34'. The viewing system 34' includes an image sensing device 50 which may be provided for example as a charge coupled device. The viewing path further includes an objective lens 52 and a window 54 disposed in an aperture of the viewing path 37. The image sensing device 50 is coupled through a plurality of wires 51 to an electrical cable 48 which may couple the image sensing device 50 to a signal processor as is generally known. The electrical viewing system 34' may also be provided as one of the types described in co-pending patent application Ser. No. 07/967,996 filed on Oct. 28, 1992 having Koichiro Hori as a named inventor and incorporated herein by reference.

Having described preferred embodiments of the invention, it will now become apparent to one of skill in the art that other embodiments incorporating the concepts may be used. It is felt, therefore, that these embodiments should not be limited to disclosed embodiments but rather should be limited only by the spirit and scope of the appended claims.

What is claimed is:

1. An endoscope comprising:
   a tube having first and second ends and having a bore therethrough;
   a sheath, installable over said tube, said sheath having a first end and a second end;
   a handle body having first and second ends, said handle body coupled to the first end of said tube, said handle body having a channel extending between the first and second ends of said handle body wherein at least one side of the channel is open along substantially the entire length thereof to promote cleaning of the channel;
   a cover having an interlocking fit with the channel of said handle body wherein at least a portion of said cover projects into the channel of said handle body; and
   an end piece coupled to said handle body, said end piece for introducing fluid into the channel coupled to said handle body.

2. The endoscope of claim 1 wherein:
   said tube includes a viewing system.

3. The endoscope of claim 2 wherein said tube includes means for illuminating an external region about the second end of said tube.

4. The endoscope of claim 3 wherein:
   a first one of said first and second tube ends is provided having a connecting portion; and
   a corresponding one of the first and second sheath ends is provided having a connecting portion provided to mate with the connecting portion of said tube.

5. The endoscope of claim 4 wherein said tube is provided having a channel, which is exposed when said sheath is disengaged from said tube.

6. The endoscope of claim 5 wherein said viewing system is provided as an electronic viewing system.

7. The endoscope of claim 5 wherein said viewing system is provided as an optical viewing system.

8. An endoscope comprising:
   a handle body having a bottom wall with an aperture provided therein and a pair of side walls wherein said side walls extend from opposing sides of said bottom wall and provide a channel region within said handle body wherein the channel region is exposed along at least one surface of said handle body;
   a cover, having first and second surfaces and having a shape selected to provide an interlocking fit with the channel of said handle body;
   a tube having a proximal end and a distal end wherein the proximal end of said tube is coupled to a first end of said handle body and wherein said tube is provided having a channel of a predetermined cross-sectional shape wherein at least one side of the channel is open to promote cleaning; and
   a sheath disposed over said tube in a region of the channel, wherein said sheath is provided having a length corresponding to the length of the channel and covers substantially all of the channel.

9. The endoscope of claim 8 wherein said sheath has a connecting portion which mates with a corresponding connecting portion disposed on a second end of said handle body.

10. The endoscope of claim 9 further comprising an end piece, wherein said end piece includes a first means for introducing a fluid into the channel of said tube and a second means, coupled to said first means, for controlling the flow of fluid into the channel of said tube.

11. The endoscope of claim 10 wherein said end piece further includes an aperture through which an instrument may be disposed through said handle body and into the channel of said tube.

12. The endoscope of claim 11 wherein said end piece has a connecting portion which mates with a corresponding connecting portion disposed on said first end of said handle body.

13. The endoscope of claim 10 further comprising an electronic viewing system.

14. The endoscope of claim 10 further comprising an optical viewing system, said optical viewing system including a plurality of lenses.

15. A cleanable operative endoscope comprising:
   a handle body having first and second ends and having a bottom wall and a pair of side walls extending from opposing sides of said bottom wall to provide a channel region of predetermined width, wherein said channel is provided for transporting irrigation fluid from the first end to the second end of said handle and for providing a path through which an instrument may be disposed, the channel being exposed along a length thereof on at least one side of said handle body through an aperture having a predetermined shape;
   a cover disposed on said handle body, said cover having first and second opposing surfaces wherein said cover is provided having a boss projecting from a first surface thereof, wherein said boss is provided having a shape substantially corresponding to the shape of the aperture in said handle body and wherein said cover is disposed on said handle body such that the boss is disposed through the aperture and into at least a portion of the channel;
   an end piece disposed over the first end of said handle body;
   a cylindrical tube having a proximal end and a distal end wherein:
      the proximal end of said cylindrical tube is coupled to the second end of said handle body;
      said cylindrical tube has a channel extending along a first surface of said cylindrical tube between the proximal and the distal tube ends, said channel having a semicircular cross sectional shape; and
      a plurality of fiber optic rods are disposed in said cylindrical tube, wherein said plurality of fiber optic rods are disposed in an annulus about said cylindrical tube and each of said fiber optic rods has a first end and a second end, said second end of said fiber optic rods terminated at the distal end of said cylindrical tube; and
   a sheath disposed over said cylindrical tube and removably coupled to a first one of said cylindrical tube and the second end of said handle body such that said sheath may be removed to expose the channel in said cylindrical tube, wherein said sheath is provided having a length corresponding to the length of the channel and covers substantially all of the channel.

16. The endoscope of claim 15 wherein the second end of said handle body is provided having a threaded connector and said sheath is provided having a corresponding threaded connector such that said sheath may be coupled to said handle body via said threaded connectors.

17. The endoscope of claim 16 wherein said end piece is provided having a fluid injection port for injecting irrigation fluid into the channel of said cylindrical tube and an instrument insertion aperture having a diameter such that a medical instrument may be disposed therethrough and into said cylindrical tube.

18. The endoscope of claim 17 wherein the first end of said handle body is provided having a threaded connector and said end piece is provided having a corresponding threaded connector such that said end piece may be coupled to the first end of said handle body via said threaded connectors.

19. The endoscope of claim 18 further comprising a viewing system disposed in a bore along a longitudinal axis of said cylindrical tube wherein said viewing system is provided as an electronic viewing system, said electronic viewing system including an electronic image sensing device disposed in the distal end of said cylindrical tube.

20. The endoscope of claim 18 further comprising a viewing system disposed in a bore along a longitudinal axis of said cylindrical tube wherein said viewing system is provided as an optical viewing system, said optical viewing system including a plurality of lenses.

* * * * *